United States Patent
Barmore et al.

(12)

(10) Patent No.: US 6,297,508 B1
(45) Date of Patent: Oct. 2, 2001

(54) METHOD OF DETERMINING AUTHENTICITY OF A PACKAGED PRODUCT

(75) Inventors: Charles R. Barmore, Moore; Narender P. Luthra, deceased, late of Simpsonville, both of SC (US), by Pam Luthra, legal representative

(73) Assignee: Cryovac Inc., Duncan, SC (US)

( * ) Notice: Subject to any disclaimer, the term of this patent is extended or adjusted under 35 U.S.C. 154(b) by 0 days.

(21) Appl. No.: 09/369,914

(22) Filed: Aug. 6, 1999

Related U.S. Application Data

(60) Provisional application No. 60/095,911, filed on Aug. 10, 1998.

(51) Int. Cl.$^7$ .................................................. G01T 21/63
(52) U.S. Cl. ........................................................ 250/459.1
(58) Field of Search ................................ 250/372, 459.1, 250/461.1, 462.1, 365

(56) References Cited

U.S. PATENT DOCUMENTS

| | | |
|---|---|---|
| 3,279,826 | 10/1966 | Rudershausen et al. . |
| 3,530,075 | 9/1970 | Wiebe . |
| 3,666,946 | 5/1972 | Trinble . |
| 3,747,755 | 7/1973 | Senturia et al. . |
| 3,772,099 | 11/1973 | Ryan et al. . |
| 4,146,792 | * 3/1979 | Stenzel et al. ...................... 250/365 |
| 4,157,784 | 6/1979 | Grottrup et al. . |
| 4,183,989 | 1/1980 | Tooth . |

(List continued on next page.)

FOREIGN PATENT DOCUMENTS

| | | |
|---|---|---|
| 15 99 011 B2 | 7/1979 | (DE) . |
| 0 506 000 A1 | 10/1992 | (EP) . |
| 0 607 048 A1 | 7/1994 | (EP) . |
| 363881 | 12/1931 | (GB) . |
| 1123274 | 8/1968 | (GB) . |
| 1143362 | 2/1969 | (GB) . |
| 1170965 | 11/1969 | (GB) . |
| 1228388 | 4/1971 | (GB) . |
| 1231215 | 5/1971 | (GB) . |
| 1316528 | 5/1973 | (GB) . |
| 1399007 | 6/1975 | (GB) . |
| 1439173 | 6/1976 | (GB) . |
| 1482760 | 8/1977 | (GB) . |
| 2 076 337 A | 12/1981 | (GB) . |
| 2 095 822 A | 10/1982 | (GB) . |
| 2 217 838 A | 11/1989 | (GB) . |
| 59-17683 | 1/1984 | (JP) . |
| WO 81/03507 | 12/1981 | (WO) . |
| WO 81/03508 | 12/1981 | (WO) . |
| WO 94/11126 | 5/1994 | (WO) . |
| 94/16902 | 8/1994 | (WO) . |

*Primary Examiner*—Constantine Hannaher
*Assistant Examiner*—Albert Gagliarol

(57) ABSTRACT

A method of verifying the authenticity of a packaged product involves providing a package that includes a product, a packaging material covering at least one surface of the product, and at least two fluorescent materials, which (a) each can be disposed in or on the packaging material, (b) each can be disposed in or on at least one surface of the product, or (c) can be separated so that at least one of them is disposed in or on the packaging material and at least one of them is disposed in or on at least one surface of the product. The package is exposed to excitation radiation including one or more wavelengths in the range of from about 250 to about 400 nm, the luminescent radiation emitted by said fluorescent materials is spectroscopically detected in the wavelength range of about 300 to about 475 nm, and an intensity versus wavelength plot of the emitted radiation over at least a portion of the range of wavelengths detected is compiled. This compiled plot is compared against a previously measured, stored emitted radiation intensity versus wavelength plot from an authenticated standard so as to determine whether the packaged product is authentic.

20 Claims, 1 Drawing Sheet

U.S. PATENT DOCUMENTS

| | | |
|---|---|---|
| 4,186,020 | 1/1980 | Wachtel . |
| 4,202,491 | 5/1980 | Suzuki . |
| 4,219,599 | 8/1980 | Idelson et al. . |
| 4,238,524 | 12/1980 | LaLibiberte et al. . |
| 4,442,170 | 4/1984 | Kaule et al. . |
| 4,451,521 | 5/1984 | Kaule et al. . |
| 4,451,530 | 5/1984 | Kaule et al. . |
| 4,469,725 | 9/1984 | Fischer et al. . |
| 4,500,116 | 2/1985 | Ferro et al. . |
| 4,544,183 | 10/1985 | Parkinson . |
| 4,567,370 | 1/1986 | Falls . |
| 4,598,205 * | 7/1986 | Kaule et al. ................ 250/458.1 |
| 4,715,623 | 12/1987 | Roule et al. . |
| 4,736,425 | 4/1988 | Jalon . |
| 4,767,205 | 8/1988 | Schwartz et al. . |
| 4,791,449 | 12/1988 | Foley et al. . |
| 4,833,311 | 5/1989 | Jalon . |
| 4,874,188 | 10/1989 | Gravisse et al. . |
| 4,897,300 | 1/1990 | Boehm . |
| 4,992,204 | 2/1991 | Kluger et al. . |
| 5,005,873 | 4/1991 | West . |
| 5,040,889 | 8/1991 | Keane . |
| 5,055,695 | 10/1991 | Lange . |
| 5,110,530 | 5/1992 | Havens . |
| 5,118,349 | 6/1992 | Jalon . |
| 5,134,291 | 7/1992 | Ruhl, Jr. et al. . |
| 5,135,569 | 8/1992 | Mathias . |
| 5,160,826 | 11/1992 | Cohen et al. . |
| 5,201,921 | 4/1993 | Luttermann et al. . |
| 5,202,686 | 4/1993 | Rapp et al. . |
| 5,206,510 | 4/1993 | Wolfe et al. . |
| 5,209,513 | 5/1993 | Batelli . |
| 5,214,286 | 5/1993 | Milosevic et al. . |
| 5,225,679 | 7/1993 | Clarke et al. . |
| 5,255,070 | 10/1993 | Pollak et al. . |
| 5,289,547 | 2/1994 | Ligas et al. . |
| 5,298,310 | 3/1994 | Havens . |
| 5,329,127 | 7/1994 | Becker et al. . |
| 5,338,935 | 8/1994 | Truett et al. . |
| 5,418,855 | 5/1995 | Liang et al. . |
| 5,449,200 | 9/1995 | Andric et al. . |
| 5,450,190 | 9/1995 | Schwartz et al. . |
| 5,456,498 | 10/1995 | Greene . |
| 5,510,199 | 4/1996 | Martin . |
| 5,510,619 | 4/1996 | Zachmann et al. . |
| 5,537,486 | 7/1996 | Stratigos et al. . |
| 5,554,842 | 9/1996 | Connell et al. . |
| 5,573,584 | 11/1996 | Ostertag et al. . |
| 5,574,790 | 11/1996 | Liang et al. . |
| 5,640,463 | 6/1997 | Csulits . |
| 5,644,352 | 7/1997 | Chang et al. . |
| 5,667,249 | 9/1997 | Critelli . |
| 5,667,317 | 9/1997 | Tan . |
| 5,679,959 | 10/1997 | Nagase . |
| 5,685,570 | 11/1997 | Gray et al. . |
| 5,763,891 * | 6/1998 | Yoshinga et al. ............ 250/459.1 |
| 6,005,960 * | 12/1999 | Moore ............................. 382/111 |
| 6,054,021 * | 4/2000 | Kurrle et al. .................... 162/150 |
| 6,165,609 * | 12/2000 | Curatolo ........................ 426/343 |

\* cited by examiner

METHOD OF DETERMINING AUTHENTICITY OF A PACKAGED PRODUCT

This application claims the benefit of provisional application No. 60/095,911, filed on Aug. 10, 1998.

BACKGROUND INFORMATION

1. Field of the Invention

The present invention relates generally to a method of determining the authenticity of packaged products and, specifically, to the detection and analysis of radiation emitted by fluorescent materials to determine whether or not a packaged product is authentic.

2. Background of the Invention

Throughout history, extensive efforts have been undertaken in attempts to ensure that certain valuable documents and objects were genuine. Measures employed have ranged from wax seals impressed with the signets of monarchs to, in more recent times, devices such as holograms, water marks, microreplicated patterns, and the like. Especially with respect to documents such as negotiable instruments, numerous measures involving printing techniques, special inks and/or dyes, fluorescent materials, and the like have been employed. For a succinct overview of such measures, the reader is directed to the Background of the Invention section of U.S. Pat. No. 5,644,352 (Chang et al.), as well as the documents cited therein.

Relatively recently, products displayed and sold from store shelves have become of more interest to counterfeiters. One class of such valuable, yet easily duplicated products is computer software. Much time, energy, and intellect is expended in creating such products, yet a counterfeiter can reproduce such products in a short amount of time and without expending much effort or money. Accordingly, anti-counterfeit measures have become of great interest to developers and manufacturers of products such as computer software.

One of the first measures employed in efforts to thwart counterfeiters involved holograms; however, after a relatively short amount of time, counterfeiters were able to reproduce such holograms with relative ease. More recently, microreplicated patterns have been employed. While these are much harder to produce, one wishing to verify the authenticity of a product on a store shelf needs to inspect each product individually. This type of inspection often can be slow and labor intensive. Further, microreplicated patterns can involve additional costs because the authenticity feature is not incorporated into an existing part of the packaged product in question.

Retail products such as computer software often come packaged in a paperboard box sealed in a thermoplastic film. Because the type of film used to wrap such packages often is relatively simple (e.g., a single-layer polyethylene film), counterfeiters have little problem finding converters who can take polymeric resin(s), make simple films, and seal the film around the counterfeit product made by the counterfeiter.

Some have suggested that incorporating photoluminescent materials (e.g., phosphorescers and fluourescers) into packaging materials might provide an easily verifiable authenticating feature useful with regard to retail products. However, as with holograms, this type of authentication is not difficult to reproduce once the counterfeiter is aware of the presence of a photoluminescer and identifies the particular material used. Despite this potential limitation, efforts to make authentication through the use of photoluminescent materials a viable alternative continue.

A type of photoluminescent authentication is described in U.S. Pat. No. 5,005,873 (West). That reference teaches incorporating two photoluminescent materials into a film which can be laminated on a substrate such as, for example, a credit card. The laminated substrate is authenticated by exposing it to a wavelength of ultraviolet (UV) light and visually inspecting the color of visible light emitted by the photoluminescent material. Once the first inspection is complete, the laminated substrate is exposed to a different wavelength of UV light and again visually inspected to determine whether a second, different color is emitted. (Although fluorescence is referenced as the applicable emission phenomenon throughout this reference, the fact that the photoluminescent emission occurs in the visible portion of the spectrum as well as the length of time that emission is said to occur, i.e., sufficiently long to allow for visual inspection, both seem to indicate that the process involved is phosphorescence rather than fluorescence.) However, the sequential irradiation-inspection taught by this reference does not seem capable of being adapted into an easily repeatable, perhaps automated, authentication technique.

Although not concerned with the authentication of documents or retail products, U.S. Pat. No. 5,201,921 (Lutterman et al.) and U.S. Pat. No. 5,329,127 (Becker et al.) both teach the incorporation of fluorescent materials into plastic materials. Both patents are concerned with a method of labeling different plastics so that the materials can be identified and separated automatically for purposes of recycling. The former teaches the incorporation of 0.005 to 10 parts per million (ppm) of a fluorescent marker into a plastic material. By designating a particular fluorescent material to a given type of plastic material, one can automate a process for separating a variety of plastic materials for recycling purposes by, for example, exposing the plastic materials to radiation that includes wavelengths that excite the fluorescent materials, looking for a given wavelength of emitted radiation, and selecting the plastic materials with the emitted the particular wavelength of interest. The latter patent expands on this recycling automation idea by teaching the incorporation of a plurality of fluorescent materials into each plastic material, then confirming/rejecting a particular material based on the combined emission spectrum it produces when exposed to excitation radiation. The use of a plurality of fluorescers is said to overcome the relatively limited number of available dyes. After exposing a plastic material to a single radiation source, the excited component fluorescent materials emit for different lengths of time. This difference in emission duration is used to distinguish the fluorescent materials and to identify the plastic material in which they are located.

That which has not been described previously, and remains highly desirable to the manufacturers of valuable retail products such as computer software, is a method of packaging such products so that they include one or more markers that can be used to determine, in an easy and rapid manner, the authenticity of the product so packaged. Preferably, such a method would be capable of being performed while the product is in a retail setting.

SUMMARY OF THE INVENTION

Briefly, the present invention provides a method of verifying the authenticity of a packaged product. In this method, one provides a package that includes a product, a packaging material covering at least one surface of the product, and more than 10 up to about 50,000 ppm, independently, of at least two fluorescent materials which are capable of excitation by radiation in the wavelength range of about 250 to about 400 nm and are capable of emission of radiation in the wavelength range of about 300 to about 475 nm. The fluorescent materials (a) each can be disposed in or on the packaging material, (b) each can be disposed in or on at least one surface of the product, or (c) can be separated so that at least one of them is disposed in or on the packaging material and at least one of them is disposed in or on at least one surface of the product. The package is exposed to a source of excitation radiation which includes wavelengths in the range of about 250 to about 400 nm so that the fluorescent materials are excited, the fluorescent radiation emitted by the fluorescent materials is spectroscopically detected in the wavelength range of about 300 to about 475 nm, and an intensity versus wavelength plot of the emitted radiation over at least a portion of the range of wavelengths detected is compiled. This compiled plot is compared against a previously measured, stored spectrum (i.e., a plot of intensity versus wavelength of emitted radiation) from an authenticated standard so as to determine whether the packaged product is authentic.

Advantageously, the process of the present invention does not rely on a user-operator determining the presence or absence of emitted radiation and/or distinguishing the colors of two sequentially emitted wavelengths of radiation. Instead, the process of the present invention can employ an easily automated comparison of sample and standard emission spectra (i.e., intensity vs. wavelength plots). The comparison can involve, for example, complete spectrum matching or a determination of ratio of heights of emission maxima. The latter technique has the advantage of allowing for differences in the amount of fluorescent materials added batch-to-batch to the resin blends from which the thermoplastic film is made.

Also, the process of the present invention is more discriminating than standard yes/no detection methods which look only for the presence of certain wavelengths of emission. Even if a counterfeiter were to determine the types of fluorescent materials that a given manufacturer had chosen to distinguish its goods, the process of the present invention still is capable of identifying the counterfeiter's goods as inauthentic where care has not been taken to ensure that those fluorescent materials were added in the proper amounts and/or ratio.

Further, the process of the present invention does not require sophisticated detection methods and/or electronics. Instead, presently available techniques are adapted to provide a novel, beneficial authentication process.

Still further, by employing a combination light source-detector which is portable, the process of the present invention can be adapted readily for use in a retail environment. Specifically, the process of the present invention can provide a user a portable means of verifying the authenticity of items on a retail display and get an immediate readout as to whether the items are authentic. Thus, retail display verification on a commercial scale becomes feasible because a user can authenticate/reject a large number of products very rapidly.

DETAILED DESCRIPTION OF ILLUSTRATIVE EMBODIMENTS

Figure 1:
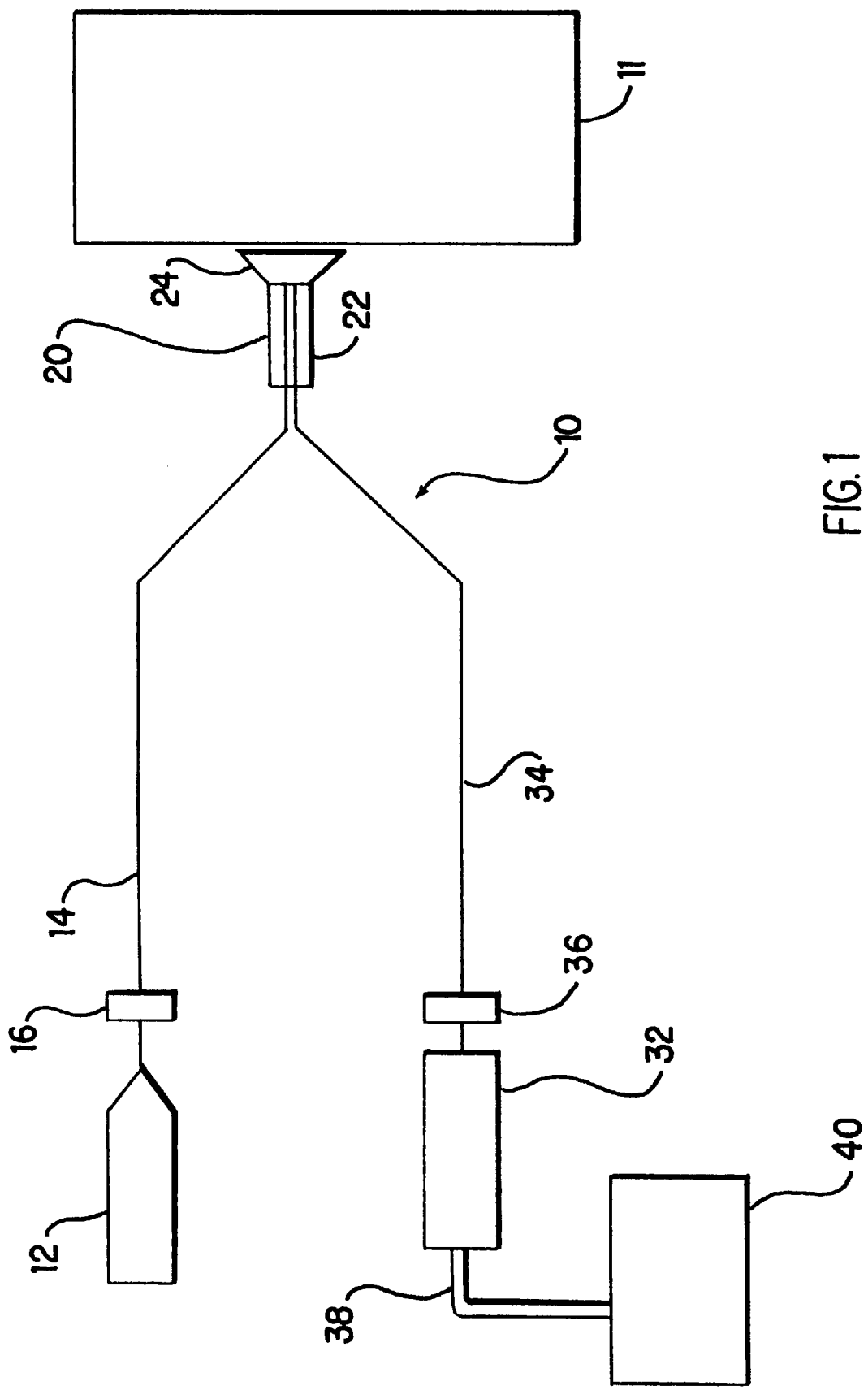
FIG. 1 is schematic view of one embodiment of the process according to the present invention.

To assist in understanding the description of the invention that follows, provided immediately are certain definitions which apply hereinthroughout unless a contrary intention is explicitly indicated:

"disposed on," with respect to the location of a fluorescent material in relation to a packaging material or product, means coated on or applied to such that it is in intimate contact with at least one primary surface of the packaging material or product;

"disposed in," with respect to the location of a fluorescent material in relation to a packaging material or product, means dispersed throughout or in one or more discreet layers of the packaging material (e.g., located in one layer of a multilayer film) or, in some manner, incorporated into a UV transparent portion of the product;

"flexible" means capable of deformation without catastrophic failure;

"polymer" means the polymerization product of one or more monomers and is inclusive of homopolymers, copolymers, and interpolymers as well as blends and modifications thereof;

"mer unit" means that portion of a polymer derived from a single reactant molecule; for example, a mer unit from ethylene has the general formula

"homopolymer" means a polymer consisting essentially of a single type of repeating mer unit;

"copolymer" means a polymer that includes mer units derived from two reactants (normally monomers) and is inclusive of random, block, segmented, graft, etc., copolymers;

"interpolymer" means a polymer that includes mer units derived from at least two reactants (normally monomers) and is inclusive of copolymers, terpolymers, tetrapolymers, and the like;

"polyolefin" means a polymer in which some mer units are derived from an olefinic monomer which can be linear, branched, cyclic, aliphatic, aromatic, substituted, or unsubstituted (e.g., olefin homopolymers, interpolymers of two or more olefins, copolymers of an olefin and a non-olefinic comonomer such as a vinyl monomer, and the like);

"(meth)acrylic acid" means acrylic acid and/or methacrylic acid;

"longitudinal direction" means that direction along the length of a film, i.e., in the direction of the film as it is formed during extrusion and/or coating;

"transverse direction" means that direction across the film and perpendicular to the machine direction;

"free shrink" means the percent dimensional change, as measured by ASTM D 2732, in a 10 cm×10 cm specimen of film when it is subjected to heat;

as a verb, "laminate" means to affix or adhere (by means of, for example, adhesive bonding, pressure bonding, corona lamination, and the like) two or more separately made film articles to one another so as to form a multilayer structure; as a noun, "laminate" means a product produced by the affixing or adhering just described;

"directly adhered," as applied to film layers, means adhesion of the subject film layer to the object film layer, without a tie layer, adhesive, or other layer therebetween.

"between," as applied to film layers, means that the subject layer is disposed in the midst of two object layers, regardless of whether the subject layer is directly adhered to the object layers or whether the subject layer is separated from the object layers by one or more additional layers;

"inner layer" means a layer of a film having each of its principal surfaces directly adhered to one other layer of the film;

"outer layer" means a layer of a film having less than both of its principal surfaces directly adhered to other layers of the film;

"inside layer" means the outer layer of a film in which a product is packaged that is closest, relative to the other layers of the film, to the packaged product;

"outside layer" means the outer layer of a film in which a product is packaged that is farthest, relative to the other layers of the film, from the packaged product;

"barrier layer" means a film layer capable of excluding one or more gases (e.g., $O_2$);

"abuse layer" means an outer layer and/or an inner layer that resists abrasion, puncture, and other potential causes of reduction of package integrity and/or appearance quality;

"tie layer" means an inner layer having the primary purpose of providing interlayer adhesion to adjacent layers that include otherwise non-adhering polymers;

"bulk layer" means any layer which has the purpose of increasing the abuse resistance, toughness, modulus, etc., of a multilayer film and generally comprises polymers that are inexpensive relative to other polymers in the film which provide some specific purpose unrelated to abuse resistance, modulus, etc.; and "seal layer" (or "sealing layer" or "heat seal layer" or "sealant layer") means
  (a) with respect to lap-type seals, one or more outer film layer(s) involved in the sealing of the film to itself (in some circumstances, as much as the outer 75 $\mu$m of a film can be involved in the sealing of the film to itself or another layer), another film layer of the same or another film, and/or another article which is not a film, or
  (b) with respect to fin-type seals, an inside film layer of a package, as well as supporting layers within 75 $\mu$m of the inside surface of the innermost layer, involved in the sealing of the film to itself; and as a noun, "seal" means a bond of a first region of a film surface to a second region of a film surface (or opposing film surfaces) created by heating (e.g., by means of a heated bar, hot air, infrared radiation, ultrasonic sealing, etc.) the regions (or surfaces) to at least their respective softening points so as to cause bonding between polymer chains.

The process of the present invention involves a package that includes a product and a packaging material. The identity of each component can vary depending on the nature of the retail environment. For example, for purposes of the present invention, where a retail item is enclosed in only a paperboard container, the retail item is the product and the paperboard container is the packaging material; however, where that same construction is shrink wrapped in a thermoplastic film, the product-container construction becomes the product and the thermoplastic film is the packaging material.

In the process of the present invention, a plurality of fluorescent materials is used to authenticate a packaged product. The fluorescent materials can be located only in or on the packaging material, only in or on the product, or in or on both the packaging material and the product. Obviously, where the packaging material is not transparent to UV radiation (e.g., a paperboard container), one or more fluorescent materials incorporated into a product packaged therein cannot be detected. However, where the same construction just described is wrapped in another material which is substantially transparent to UV radiation (e.g., a thermoplastic film), one or more of the fluorescent materials can be included on the paperboard material (which is the "product" in that case) and/or one or more of the fluorescent materials can be included in or on the substantially transparent packaging material.

Regardless of the specific combination chosen for the disposition of the fluorescent materials (i.e., all in or on the packaging material, all in or on the product, or at least one in or on the packaging material and at least one in or on the product), most typically the fluorescent materials will be disposed in a film, which is the packaging material, and on a product. That is, it is relatively simple to disperse a fluorescent material in one or more of the layers of a packaging film which is substantially transparent to UV radiation while coating the film to dispose the fluorescent material on the film would add an additional, seemingly unnecessary, step. Similarly, most underlying products are not transparent to UV radiation, such as, for example, a paperboard box containing software, such that it would be necessary to coat the fluorescent materials on the product.

However, it is within the scope of the present invention to dispose a fluorescent material on a packaging material and to dispose a fluorescent material in a product. In the case of the packaging material, such coating of the fluorescent material on the film may be necessary when it is desirable to employ a previously manufactured film which does not contain a fluorescent material in accordance with the present invention. In the case of the product, it may be desirable to dispose the fluorescent material in the product when at least some portion of the product is substantially transparent to UV radiation, such as, for example, a substantially transparent, rigid compact disc box.

For purposes of the present invention, flexible thermoplastic films are a preferred class of packaging material. Such films can conform substantially to the shape of a packaged product. Additionally, many such films are optically transparent, thus allowing potential customers to view the product enclosed. Such films can be made by a variety of manufacturing techniques well known to the ordinarily skilled artisan. The resulting films then are classified (typically) as laminated, blown, or cast.

For certain applications, a coextruded, blown film which has been oriented, most preferably biaxially oriented, can be preferred. Orienting involves initially cooling an extruded film to a solid state (by, for example, cascading water or chilled air quenching) followed by reheating the film to within its orientation temperature range and stretching it. The stretching step can be accomplished in many ways such as by, for example, blown bubble or tenter framing techniques, both of which are known to those ordinarily skilled in the art. After being heated and stretched, the film is quenched rapidly while being maintained in its stretched configuration so as to lock in the oriented molecular configuration. This combination of elongation at elevated temperature followed by cooling causes an alignment of the polymer chains to a more parallel configuration, thereby dramatically altering the mechanical properties of the film. When an unrestrained, unannealed, oriented film subsequently is heated to (or near) its orientation temperature, the film shrinks almost to its original, i.e., pre-elongation, dimensions. Such a film is said to be heat shrinkable. For certain end use applications, a film for use as the packaging material in the process of the present invention preferably can be both biaxially oriented and heat shrinkable.

Oriented films typically are oriented in several directions, usually two directions perpendicular to one another. Orientation in the machine direction is referred to as drawing, whereas orientation in the transverse direction is referred to as stretching. For films extruded through an annular die, stretching occurs when the film is blown to produce a bubble. Thereafter, drawing occurs when the film passes through two sets of powered nip rolls, with the downstream set having a higher surface speed than the upstream set. The resulting draw ratio is the surface speed of the downstream set of nip rolls divided by the surface speed of the upstream set of nip rolls.

Oriented films for use in the process of the present invention preferably have a shrink tension of at least about 700 kPa, more preferably at least about 1050 kPa, and most preferably at least about 1400 kPa. Additionally, they can exhibit a Young's modulus (measured in accordance with ASTM D 882) of at least about 200 MPa up to about 1750 MPa.

Oriented films generally have a longitudinal (L) direction free shrink of at least 1% and a transverse (T) direction free shrink of at least about 1% (both measured at 85° C.). Where desirable for a particular application, an oriented film can have a free shrink (at 85° C.) in at least one of the L and T directions of at least 2%, at least 5%, at least 10%, at least 15%, at least 20%, at least 25%, even up to 50%. A film can be biaxially oriented and have a free shrink (at 85° C.) in each of the L and T directions of from about 1 to about 20%, more preferably from about 2 to about 15%, and even more preferably from about 3 to about 10%, and a total free shrink (L+T) of from about 2 to about 40%, preferably from about 2.5 to about 30%, more preferably from about 3 to about 20%, and still more preferably from about 5 to about 15%. For certain applications, orienting then heat setting or annealing a film so as to provide a T direction free shrink (at 85° C.) of less than 10%, more preferably less than 5%, can be preferred. Heat setting can be accomplished at a temperature from about 60° to 200° C., preferably from about 70° to 150° C., and more preferably from about 80° to 90° C.

Where a film for use in the process of the present invention is shrinkable, it preferably includes up to about 20 layers, more preferably 3 to about 12 layers (especially where the total number of layers is an odd number), although any number of layers are feasible as long as the film provides the desired properties for the particular packaging operation in which it is to be used. Regardless of the particular number or order of the film layers, those films with at least one layer that includes a polymer including mer units derived from ethylene are useful for many end use applications.

A film used as the packaging material in the process of the present invention optionally can be subjected to an energetic radiation treatment produced by, for example, corona discharge, plasma, flame, ultraviolet, X-ray, γ-ray, β-ray, or high energy electron systems so as to induce crosslinking between polymer chains. Such irradiative crosslinking of polymeric films is disclosed in, for example, U.S. Pat. No. 4,064,296 (Bornstein et al.), the teaching of which is incorporated herein by reference. Suitable levels of radiation range from about 2 to about 15 MR, preferably from about 2 to about 10 MR. As one of ordinary skill in the art can derive from the description of exemplary films infra, the precise amount of radiation can depend on the film composition, thickness, etc., as well as the desired end use. A film used in the process of the present invention can be used as or in connection with irradiated, oriented, heat set films and/or can be laminated, adhesively adhered, extrusion coated, or extrusion laminated onto a substrate to form a laminate.

Films used in the packaging industry can be categorized by the number of component layers. Some films are made from a single polymer or blend of polymers and thus have only one layer. However, most films presently used include more than one layer, i.e., are multilayer films. In general, the layers of a multilayer film can be classified as inner or outer. Additionally, any number of tie layers can be included. The number of layers present in a film used as a packaging material in the process of the present invention is unimportant. Whatever type of film has been found to be suitable for a given packaging application likely can be modified according to the teaching set forth below with respect to addition of fluorescent materials so as to be useful in the process of the present invention.

Where the packaging material used in the process of the present invention is a multilayer film, it can include those films that have one or more of the following types of layers: abuse layers, barrier layers, tie layers, bulk layers, and seal layers. The physical properties required of a film for any given end use application often determine the composition of the film and/or the compositions of the various layers of the film. Where a variety of properties are required, a variety of layers containing differing polymeric components can be, and usually are, employed. For example, the product(s) being packaged preferably is to be protected from one or more detrimental materials (e.g., atmospheric $O_2$), a layer including, for example, ethylene/vinyl alcohol interpolymer (EVOH), vinylidene chloride interpolymer, or one or more of certain polyamides (e.g., nylons) can be included in the multilayer film structure. If the barrier employed is one which is known to be sensitive to moisture, such as EVOH, and the application requires exposure of the film to moisture, then one or more moisture barrier layers also can be included. If the film is likely to be subjected to abuse during handling and/or transport, an abuse layer can be provided (either as an inner or outer layer). One or two seal layers can be provided to allow for sealing of the film to itself or another packaging article during the formation of a package. One or more inner layers also can be provided, and films with at least one inner layer are preferred for many applications.

Where a flexible film to be used in the process of the present invention is a multilayer film, those films containing at least one layer including a polymer that includes mer units derived from ethylene can be preferred for some end use applications. These polymers can be ethylene homopolymers or they also can include mer units derived from one or more of (meth)acrylic acid, a $C_3$–$C_{20}$ α-olefin, $C_1$–$C_{20}$ esters of (meth)acrylic acid, vinyl acetate, and vinyl alcohol. Ionomers also can be useful. Particularly preferred for many applications are ethylene/α-olefin interpolymers.

The relatively recent advent of single site-type catalysts (e.g., metallocenes) necessitates further definitional clarification when discussing ethylene homo- and copolymers. Heterogeneous polymers are those having relatively wide variation in molecular weight and composition distribution. Polymers prepared with, for example, conventional Ziegler Natta catalysts are heterogeneous. Such polymers can be used in a variety of layers including the seal layer(s). On the other hand, homogeneous polymers have relatively narrow molecular weight and composition distribution. Homogeneous polymers differ structurally from heterogeneous polymers in that they exhibit a relatively even sequencing of comonomers within a chain, a mirroring of sequence distribution in all chains, and a similarity of chain lengths, i.e., a narrower molecular weight distribution. Homogeneous polymers typically are prepared using metallocene or other single site-type catalysts. Homogeneous polymers also can be used in a variety of layers including the seal layer(s).

The term "ethylene/α-olefin copolymer" (or interpolymer) as used herein refers both to heterogeneous materials such as low density polyethylene (LDPE), medium density polyethylene (MDPE), linear low density polyethylene (LLDPE), and very low and ultra low density polyethylene (VLDPE and ULDPE), as well as to homogeneous materials which, in general, are prepared by the copolymerization of ethylene and one or more α-olefins. The comonomer preferably is a $C_4$–$C_{20}$ α-olefin, more preferably a $C_4$–$C_{12}$ α-olefin, still more preferably a $C_4$–$C_8$ α-olefin. Particularly preferred α-olefins include 1-butene, 1-hexene, 1-octene, and mixtures thereof. In general, from about 80 to 99 weight percent ethylene and from 1 to 20 weight percent α-olefin, preferably from about 85 to 95 weight percent ethylene and from 5 to 15 weight percent α-olefin, a copolymerized in the presence of a single site catalyst. Examples of commercially available homogeneous materials include the metallocene catalyzed Exact™ resins (Exxon Chemical Co.; Baytown, Tex.), substantially linear Affinity™ and Engage™ resins (Dow Chemical Co.; Midland, Mich.), and Tafmer™ linear resins (Mitsu Petrochemical Corp.; Tokyo, Japan).

Homogeneous ethylene/α-olefin copolymers can be characterized by one or more methods known to those of skill in the art, such as molecular weight distribution ($M_w/M_n$), composition distribution breadth index (CDBI), narrow melting point range, and single melt point behavior. Molecular weight distribution, also known as polydispersity, can be determined by, for example, gel permeation chromatography. Homogeneous ethylene/α-olefin copolymers to be used in a layer of the film of the present invention preferably have an $M_w/M_n$ of less than 2.7; more preferably from about 1.9 to 2.5; still more preferably, from about 1.9 to 2.3.

The CDBI of homogeneous ethylene/α-olefin copolymers generally is greater than about 70 percent. CDBI is defined as the weight percent of copolymer molecules having a comonomer content within 50% (i.e., ±50%) of the median total molar comonomer content. CDBI can be determined by temperature rising elution fractionation as described by, for example, Wild et al., *J. Poly. Sci.—Poly. Phys. Ed.*, vol. 20, 441 (1982). Linear polyethylene, which does not contain a comonomer, is defined to have a CDBI of 100%. CDBI determination clearly distinguishes homogeneous copolymers (CDBI values generally above 70%) from presently available VLDPEs (CDBI values generally less than 55%).

Homogeneous ethylene/α-olefin copolymers also typically exhibit an essentially single melting point with a peak melting point ($T_m$), as determined by differential scanning calorimetry (DSC), of from about 60° to 105° C., more precisely a peak $T_m$ of from about 80° to 100° C. As used herein, the phrase "essentially single melting point" means that at least about 80% (by weight) of the material corresponds to a single $T_m$ at a temperature within the range of from about 60°0 to about 105° C., and essentially no substantial fraction of the material has a peak melting point in excess of about 115° C. as determined by DSC analysis (e.g., on a Perkin Elmer™ System 7 Thermal Analysis System). The presence of higher melting peaks has been found to be detrimental to film properties such as haze and seal initiation temperature.

Of course, additives commonly included in thermoplastic films also can be included in a film used in the process of the present invention. Typical additives include antislip agents, antiblocking agents (particularly diatomaceous earth and alkali aluminosilicate ceramic microspheres), antifogging agents, and the like.

The process of the present invention can involve films made by blowing coextrusion, lamination, and casting techniques, as well as other film-forming techniques known in the art. Although this invention is not intended to be limited to a particular type or class of film structure, the types of film structures in which one or more layers might include a fluorescent material include, but are not limited to, relatively simple films such as one-, two-, and three-layer films that include one or more layers including polypropylene (including oriented and biaxially oriented polypropylene), polyethylene (including blown polyethylene), PVC, PET, and the like.

Where the packaging material of the present invention is a flexible film, it can take the form of stretch film, film suitable for vertical or horizontal form-fill-and-seal end use, lidstock film, film suitable for vacuum skin packaging, film suitable for use as a barrier bag, film suitable for use as a patch bag, film suitable for use in case ready packaging, film suitable for use in a thermoformed container (particularly in a film used as a liner in a thermoformed tray, such as a polystyrene tray), aroma/odor barrier film, film suitable for use in cook-in end use applications (especially heat shrinkable bags, heat shrinkable and non-heat shrinkable casings, and containers thermoformed from non-heat shrinkable films and sheets), and medical film. Some specific examples of such flexible film include (a) films used to produce bags such as those described in, for example, U.S. Pat. No. 3,741,253 (Brax et al.), U.S. Pat. No. 3,891,008 (D'Entremont), U.S. Pat. No. 4,048, 428 (Baird), and U.S. Pat. No. 4,284,458 (Schirmer);

(b) films used to produce bags for cook-in applications, such as those described in, for example, U.S. Pat. No. 4,064,296 (Bornstein et al.) and U.S. Pat. No. 4,855, 183 (Oberle);

(c) films used in connection with patch bags, such as those described in, for example, U.S. Pat. No. 4,755,403 (Ferguson);

(d) shrink films such as those described in, for example, U.S. Pat. Nos. 4,551,380 and 4,643,943 (both to Schoenberg);

(e) films having oxygen, moisture, or odor barrier functionality such as those described in, for example, U.S. Pat. No. 4,064,296 (Bornstein et al.), U.S. Pat. No. 4,724,185 (Shah), U.S. Pat. No. 4,839,235 (Shah), and U.S. Pat. No. 5,004,647 (Shah);

(f) films suitable for medical applications such as, for example, those described in U.S. Pat. No. 5,695,840 (both to Mueller);

(g) films suitable for use in a thermoformed package such as, for example, those disclosed in U.S. Pat. No. 4,735,855 (Wofford et al.);

(h) stretch/shrink-type films such as those disclosed in, for example, U.S. Pat. No. 4,617,241 (Mueller);

(i) films suitable for the packaging of flowable or pumpable products such as those disclosed in, for example, U.S. Pat. No. 4,746,562 (Fant);

(j) films suitable for packaging, water cooking, and storing food products such as are disclosed in, for example, U.S. Pat. No. 4,104,404 (Bieler et al.);

(k) hot blown films of a type useful in chub packaging such as are described in, for example, U.S. Pat. No. 4,937,112 (Schirmer);

(l) films having LLDPE or LMDPE in a core and/or an intermediate layer, such as those described in, for example, U.S. Pat. No. 4,532,189 (Mueller) U.S. Pat. No. 4,194,039 (Mueller), U.S. Pat. No. 4,390,385 (Ferguson et al.), U.S. Pat. No. 4,274,900 (Mueller et al.), U.S. Pat. No. 4,188,443 (Mueller et al.), and U.S. Pat. No. 5,298,302 (Boice);

(m) films having a low shrink energy such as those disclosed in, for example, U.S. Pat. No. 4,833,024 (Mueller) and U.S. Pat. No. 5,023,143 (Nelson);

(n) films suitable for use in vacuum skin packaging applications, such as those disclosed in, for example, U.S. Pat. No. 4,886,690 (Davis et al.), U.S. Pat. No. 4,963,427 (Botto et al.), and 5,075,143 (Bekele);

(o) films including one or more layers that contain a homogeneous polymer such as those disclosed in, for example, European Publication No. 0 597 502 A3 (Babrowicz et al.) as well as U.S. Pat. No. 5,604,043 (Ahlgren) and U.S. Pat. No. 5,491,019 (Kuo); and (p) films having high oxygen transmission rates such as, for example, those described in U.S. Pat. No. 5,491,019 (Kuo) and U.S. Pat. No. 5,523,136 (Fischer et al.) as well as U.S. patent application Ser. No. 08/889,000 (Mossbrook et al.).

The teachings of each of the foregoing references are incorporated herein by reference. Those of ordinary skill in the art can envision other packaging applications in which the film of the present invention can be used; these too are within the scope of the present invention.

Fluorescent materials useful in the process of the present invention include those which are capable of excitation by radiation in the wavelength range of about 250 to about 400 nm, preferably in the range of about 300 to about 350 nm, and emission of radiation in the wavelength range of about 300 to about 475 nm, preferably in the range of about 350 to about 450 nm. Materials need not have an excitation or emission maximum in the foregoing ranges (e.g., materials which are at least somewhat capable of excitation by radiation in the foregoing wavelength range but which have excitation maxima up to about 475, 500, or even 525 nm, as well as materials which are capable of at least some emission of radiation in the foregoing wavelength range but which have emission maxima up to about 500, 525, or even 550 nm, can be useful in the process of the present invention), although use of fluorescent materials which do have such maxima can be preferable. Because UV radiation generally is defined as light having a wavelength of about 10 to about 400 nm, one can see that fluorescent materials useful in the process of the present invention are capable of excitation by UV radiation and capable of emission of UV and near-UV (i.e., violet) radiation. Examples of such fluorescent materials include, but are not limited to, various stilbenes, coumarins, thioxanthones, rhodamines, benzoxazoles, azo dyes, polycyclic aromatic hydrocarbons and heterocycles including Lumogen™ dyes and pigments (BASF; Mt. Olive, N.J.), thioxazoles, decacyclene, fluoroscein, fluorene, 9-fluorenone, fluoranthene, and the like. Preferred among the foregoing are thioxazoles and polycyclic aromatics. Such materials can be in the form of solubilized or dispersed powders, dissolved liquids, dispersed microspherical particles, and the like.

Regardless of the identity of the fluorescent materials used, they are incorporated into (independently) one or both of the product and the packaging material, as discussed above. Preferably, at least some of each of the fluorescent materials is located at a position on/in the package where they are the only materials capable of fluorescence, i.e., the background therefor is spectroscopically non-emissive. For example, many types of paper and paperboard have included therein whiteners, brighteners, etc., many of which are at least somewhat fluorescent. Should the irradiation and detection steps of the process of the present invention be carried out at a location on the packaged product where such background fluorescent materials are present, the presence of such materials need to be accounted for in the comparison step of the process. (If desired, the location in question can be made to include one of the identifying, i.e., non-background, fluorescent materials.) Where the irradiation and detection steps of the process of the present invention are executed at a location on the packaged product where such background fluorescent materials are absent, their influence need not be taken into account.

The packaging material can be flexible or inflexible material, depending on the particular product to be packaged and the storage, transportation, and display requirements involved with such a product. Depending on the nature of the packaging material, the manner in which the fluorescent materials are incorporated can vary extensively. For example, where the packaging material is paperboard, standard blending, printing, and/or overcoating techniques can be used. Where the packaging material is a flexible film, blending is preferred, although printing and/or overcoating techniques also can be used. Those of ordinary skill in the art are familiar with these and other substantially identical techniques. (Of course, the manner in which the fluorescent materials can be incorporated in the product, as opposed to or in addition to the packaging material, can vary just as widely.)

The particular layer(s) of a film containing the fluorescent material and the particular amount of fluorescent material used can, of course, depend on a variety of factors including, but not limited to, the end use of the packaging material; the type of product being packaged; the sensitivity of the detector; and the number of combinations needed to distinguish various members of a class of products or to distinguish one entity's products from those of other manufacturers of like products. As a general guideline, fluorescent material can be included in a packaging material and/or the packaged product in an amount of from more than 10 up to about 50,000 ppm, preferably from about 15 to about 10,000 ppm, more preferably from about 20 to about 1000 ppm, and even more preferably from about 25 to about 200 ppm.

Where fluorescent material is to be located in the packaging material and the packaging material is a thermoplastic film, the fluorescent material can be added in a discontinuous or striped manner. This can be done according to the process described in U.S. Pat. No. 5,298,310 (Havens), the disclosure of which is incorporated herein by reference.

Where the packaging material used in the process of the present invention is a thermoplastic film, providing a film with good optical clarity (i.e., one that is essentially clear, even though it may have a minor amount of coloring and/or pearlescence depending on the particular fluorescent materials used) can be preferred for certain end use applications. For example, where the product to be packaged is a box in which an item is located (e.g., a computer software package), using an essentially clear film allows the consumer to see the product wrapped in the film.

Referring now to FIG. 1, a spectroscopic system 10 for use in the process of the present invention is shown in conjunction with product 11. Product 11 can include fluorescent materials on its outer surface, in a surrounding packaging material, or both, as described supra.

Spectroscopic system 10 is shown schematically for ease of understanding. The ordinarily skilled artisan readily can envision the scale and form of the individual components described in the paragraphs that follow. The identity and particular structure of the components are unimportant to the utility of the process of the present invention.

Spectroscopic system 10 includes an excitation portion and an emission portion which are conjoined at probe 20. The excitation portion of system 10 involves light source 12, input optical fiber 14, and optional optical filter 16. Light source 12 can be, for example, a xenon flash lamp, a mercury lamp, a deuterium bulb, or the like although any light source that reproducibly can create radiation including wavelengths in the range of about 250 to about 400 nm can be used. (For example, xenon flash lamps typically have a spectral output in the range of about 200 to about 700 nm.) Excitation radiation created by source 12 can be carried easily and efficiently to probe 20 via input optical fiber 14. Other means to convey light from one location to another (including air) are available and known; however, optical fibers are a convenient, lightweight, efficient means of doing so. If desired or necessary to minimize the wavelength of light reaching probe 20, light created by source 12 can be routed through optical filter 16 prior to entering probe 20. For example, use of a band pass filter can produce excitation radiation having a range of wavelengths limited to those of interest.

The emission portion of system 10 involves spectrometer 32, output optical fiber 34, optional optical filter 36, connector 38, and storage means 40. As the fluorescent materials in product 11 fluoresce, the emitted light is carried to spectrometer 32 by output optical fiber 34. As with input optical fiber 14, output optical fiber 34 is a convenient means to transport light from one location to another, although other equivalent means are available. Prior to entering spectrometer 32, the emitted light can be routed through optical filter 36 such as, for example, a cut-off filter. Such a filter can limit the emitted light entering spectrometer 32 to the wavelength range of interest for a given spectroscopic analysis, e.g., any subset of the range of abut 300 to about 475 nm. Output optical fiber 34 typically terminates at spectrometer 32 in the immediate vicinity of, or optically connected to, a detector such as a photomultiplier tube. Output from the detector (not shown) can be fed from spectrometer 32 to storage means 40 through connector 38, typically a coaxial cable. Storage means 40 can be any analog or digital data storage system such as, for example, a notebook-style personal computer, a desktop personal computer, a magnetic recording medium, or the like.

The excitation and emission portions of spectroscopic system 10 come together at probe 20, which generally includes a housing 22 and an optical shield 24. Housing 20 encloses and protects input optical fiber 14 and output optical fiber 34. By forming housing 22 into a shape that fits an operator's hand, the two optical fibers easily can be brought into close proximity with product 11. For example, housing 22 can take the shape of a pistol or handle grip. Optional shield 24 can aid in minimizing the amount of stray radiation reaching output optical fiber 34 although, as one skilled in the art can see, housing 22 can be formed in such a way that optical shield 24 becomes superfluous.

Although storage means 40 merely can receive and hold data to be analyzed (by, for example, a separate computing device), it preferably is capable of compiling and displaying the output spectroscopic data. Regardless of whether or not accomplished by storage means 40, an intensity versus wavelength plot of the emitted radiation over at least a portion of the range of wavelengths detected is compiled. This can be done by means of computer software programs in common use with UV-visible spectroscopic equipment. The compiled intensity vs. wavelength plot is compared against a previously measured, stored spectrum (i.e., emitted radiation intensity vs. wavelength plot) from an authenticated standard so as to determine whether the packaged product is authentic. This comparison can be performed manually; however, the comparison preferably is done by means of a computer. (Advantageously, many spectrum compilation programs also can compare detected spectra against stored spectra; thus, the need for separate software programs is eliminated.) Compiling a normalized, authenticated standard from a series of spectra taken on an authentic sample can prove beneficial by, for example, eliminating stray anomalous results.

The comparison of spectra can involve, for example, comparing intensity values at one or more wavelengths, a determination of ratio of emission intensity maxima at two or more wavelengths, complete spectrum matching, or the like. The ratio matching technique has the advantage of allowing for batch-to-batch differences in the amount of fluorescent materials added to the resin blends from which the thermoplastic film is made. Where a particular type of thermoplastic film is made by, for example, coextruding resins into a multilayer structure, one or more of those resin sources can include the aforementioned fluorescent materials. Each time that the particular type of film is made, the amount of fluorescent materials incorporated into the resin source(s) during the preceding manufacturing runs might not be able to be replicated exactly. However, the ratio of fluorescent materials can be maintained by pre-blending the fluorescent materials into a master batch and then adding approximately the same amount of master batch each time film is to be made.

Advantageously, the electronics utilized in UV radiation sources and detectors have improved to the point where such sources and detectors can be combined in a single portable unit which is capable of being transported to remote locations (e.g., a store or a warehouse). When such a portable unit is used, the process of the present invention can be adapted for use where the product being authenticated is in a retail setting. Specifically, a user-operator can use such a portable unit in a relatively confined area such as, for example, a row of display shelves in a typical retail setting. Once one product has been authenticated/rejected, another product is exposed to exciting UV radiation and authenticated/rejected.

As is obvious from the foregoing description, the identity of the product to be packaged is relatively unimportant. Any goods which have intrinsic value and are susceptible to copying or counterfeiting can benefit from the authentication process of the present invention. Examples include, but are not limited to, computer software, perfumes, official documents, and the like.

Objects and advantages of this invention are further illustrated by the following examples. The particular materials and amounts thereof, as well as other conditions and details, recited in these examples should not be used to unduly limit this invention.

EXAMPLES

Examples 1–8

A series of three-layer heat shrinkable films were made by coextrusion followed by biaxial orientation according to procedures known in the art. Each of the films had outer layers made from a blend of ethylene/vinyl acetate copolymer (EVA), LDPE, and LLDPE, while the inner layer was made from LLDPE.

Each time that a film was made, a different combination of three fluorescent dyes was mixed into the EVA/LDPE/LLDPE blend from which one of the outer layers was made. The dyes used were A) Uvitex™ optical brightener (Ciba-Geigy Corp.; Greensboro, N.C.), B) Lumogen™ red dye, and C) decacyclene.

The amounts of each dye used in the various films was as shown in Table 1, immediately below.

TABLE 1

| Sample no. | Amount of A (ppm) | Amount of B (ppm) | Amount of C (ppm) |
|---|---|---|---|
| 1 | 25 | 15 | 50 |
| 2 | 50 | 30 | 100 |
| 3 | 100 | 30 | 0 |
| 4 | 200 | 30 | 100 |
| 5 | 50 | 30 | 200 |
| 6 | 0 | 30 | 200 |
| 7 | 50 | 30 | 0 |
| 8 | 100 | 60 | 200 |

Using standard spectroscopic equipment, several fluorescence spectra of each film sample were taken and electronically stored so as to provide a standard for each film. Thereafter, the films were tested in a random fashion and each could be identified based on comparisons against the stored spectra.

This shows that the process of the present invention can be used to differentiate among several types of similar films (e.g., ones incorporating the same fluorescent dyes but in various ratios). By assigning a given fluorescent dye-containing film formulation to a given product to be packaged, the authenticity of that product can be verified in a simple and rapid fashion.

Example 9

A standard piece of paperboard was coated with Uvitex™ optical brightener and wrapped in a thermoplastic film which included another fluorescent material. This sample was spectroscopically analyzed in the manner described with respect to Examples 1–8. The spectrum of the film-paperboard combination was able to be matched to a reference spectrum of a film which included both the Uvitex™ optical brightener and the same other fluorescent material.

The foregoing shows that the process of the present invention can be effective even where one or more of the fluorescent materials is incorporated into a material (e.g., the product) underlying a thermoplastic packaging material (e.g., a packaging film) incorporating one or more other fluorescent materials.

We claim:

1. A method of verifying the authenticity of a packaged product, comprising:
   a) providing a package which comprises
   1) a product,
   2) a packaging material covering at least one surface of said product, and
   3) more than 10 up to about 50,000 parts per million independently of at least two fluorescent materials, said fluorescent materials being capable of excitation by radiation in the wavelength range of about 250 to about 400 nm and emission of radiation in the wavelength range of about 300 to about 475 nm, wherein one of the following is true:
      (a) each of said fluorescent materials is disposed in or on said packaging material,
      (b) each of said fluorescent materials is disposed in or on at least one surface of said product, or
      (c) at least one of said fluorescent materials is disposed in or on said packaging material and at least one of said fluorescent materials is disposed in or on at least one surface of said product;
   b) exposing said package to a source of excitation radiation comprising wavelengths in the range of about 250 to about 400 nm so that said fluorescent materials are excited by said excitation radiation;
   c) spectroscopically detecting the radiation emitted by said fluorescent materials in the wavelength range of about 300 to about 475 nm;
   d) compiling an intensity versus wavelength plot of said emitted ultraviolet radiation over at least a portion of the range of wavelengths detected; and
   e) comparing said compiled intensity versus wavelength plot against a previously measured, stored intensity versus wavelength plot of an authenticated standard so as to determine whether said packaged product is authentic.

2. The method of claim 1 wherein the comparison of said intensity versus wavelength plots involves comparing intensity values at one or more wavelengths.

3. The method of claim 1 wherein the comparison of said intensity versus wavelength plots involves comparing ratios of intensity values at two or more wavelengths.

4. The method of claim 1 wherein each of said fluorescent materials is disposed in said packaging material.

5. The method of claim 4 wherein each of said fluorescent materials is present in said packaging material in an amount of from about 15 to about 10,000 parts per million.

6. The method of claim 1 wherein each of said fluorescent materials is disposed in or on at least one surface of said product.

7. The method of claim 1 wherein at least one of said fluorescent materials is disposed in said packaging material and at least one of said fluorescent materials is disposed on at least one surface of said product.

8. The method of claim 7 wherein said at least one fluorescent material disposed in said packaging material is present in an amount of from about 15 to about 10,000 parts per million.

9. The method of claim 1 wherein at least one of said at least two fluorescent materials has a wavelength of maximum excitation in the range of between about 300 and about 350 nm.

10. The method of claim 1 wherein at least one of said at least two fluorescent materials has a wavelength of maximum emission in the range of between about 350 and about 450 nm.

11. The method of claim 1 wherein said packaging material is essentially clear.

12. The method of claim 11 wherein said excitation radiation is focused on said package at a location where said product provides a spectroscopically non-emissive background, with the proviso that said location may include one or more of said at least two fluorescent materials.

13. The method of claim 1 wherein said spectroscopic detection is provided by a photomultiplier tube.

14. The method of claim 1 wherein said excitation radiation comprises at least one wavelength in the range of between about 300 and about 350 nm.

15. The method of claim 1 wherein at least one of said fluorescent materials is disposed in said packaging material, said at least one fluorescent material being disposed in a discontinuous manner.

16. The method of claim 1 wherein said packaging material is a thermoplastic film.

17. The method of claim 16 wherein said thermoplastic film comprises at least one layer comprising a polymer comprising mer units derived from ethylene.

18. The method of claim 17 wherein said thermoplastic film is oriented.

19. The method of claim 16 wherein said thermoplastic film is oriented.

20. The method of claim 19 wherein said oriented thermoplastic film is shrunk about said product.

* * * * *